United States Patent [19]
Kelly et al.

[11] Patent Number: 6,074,865
[45] Date of Patent: Jun. 13, 2000

[54] RECOMBINANT DENGUE VIRUS DNA FRAGMENT

[75] Inventors: Eileen P. Kelly, Takoma Park, Md.; Alan D. King, Washington, D.C.

[73] Assignee: The United States of America as represented by the Secretary of the Army, Washington, D.C.

[21] Appl. No.: 08/504,878

[22] Filed: Jul. 20, 1995

[51] Int. Cl.$^7$ .......................... C07H 21/04; C12N 15/85; C12N 7/00; C12N 15/00

[52] U.S. Cl. ...................... 435/235; 435/320.1; 435/325; 536/23.1

[58] Field of Search .......................... 536/23.1; 424/93.1, 424/192.1, 199.1, 204.1; 530/395; 435/235, 320.1, 325

[56] References Cited

PUBLICATIONS

Putnak et al. Dengue–1 virus envelope glycoprotein gene expressed in recombinant baculovirus elicits–neutralizing antibody in mice and protects them from virus challenge. Am. J. Trop. Med. Hyg. 45: 159–167, 1991.

Delenda et al. Analysis of C–terminally truncated denuge 2 and dengue 3 virus envelope glycoproteins: processing in insect cells and immunogenic properties in mice. J. Gen. Virol. 75: 1569–1578, 1994.

Men et al. Carboxy–terminally truncated dengue virus envelope glyrproteins expressed on the cell surface and secreted extracellularly exhibit increased immunogenicity in mice. J. Virol. 65: 1400–1407, 1991.

Deubel et al. Processing, secretion, and immunoreactivity of carboxy terminally truncated dengue–2 virus envelope proteins expressed in insect cells by recombinant baculovirus. Virology 190: 442–447, 1991.

Zhang et al. Immunization of mice with dengue structural proteins and nonstructural protein NS1 expressed by baculovirus recombinant induces resistance to dengue virus encephalitis. J. Virol. 62: 30227–3031, 1988.

Eckels et al. Immunization of monkeys with baculovirus–dengue type–4 recombinants containing envelope and nonstructural proteins: evidence of priming and partial protection. Am. J. Trop. Med. Hyg. 50: 472–478, 1994.

Hahn et al Virology.162:167–180, 1988.

Delenda et al Arch. Virol. 139:197–207, 1994.

Venugopal et al Vaccine 12(11):966–976, 1994.

Chen et al. A simple and rapid method of preparing large fragments of dengue virus cDNA from replicative–form RNA using reverse transcriptase and PCR. Journal of Virological Methods, vol. 39, pp. 197–206, Sep. 1992.

Pincus et al. Recombinant vaccinia virus producing the prM and E proteins of yellow fever virus protects mice ftom lethal yellow fever encephalitis. Virology, vol. 187, pp. 290–297, Mar. 1992.

Markoff, L. In vitro Processing of Dengue Virus Structural Proteins: Cleavage of the Pre–Membrane Protein. J. Virology 63:3345–3352, 1989.

*Primary Examiner*—Bruce R. Campell
*Assistant Examiner*—Deborah J. R. Clark
*Attorney, Agent, or Firm*—Charles H. Harris; John Francis Moran

[57] ABSTRACT

A recombinant protein encompassing the complete envelope glycoprotein and a portion of the carboxy-terminus of the membrane/premembrane protein of dengue 2 virus was expressed in baculovirus as a protein particle. The recombinant protein particle was purified and found to provide protection against lethal challenge with dengue 2 virus in mice.

20 Claims, 7 Drawing Sheets

Figure 1. Illustration of the pBlueBacIII shuttle vector and gene sequences used for expression of the dengue 2 virus envelope glycoprotein in insect cells.

Figure 2. Gel filtration of dengue 2 recombinant envelope glycoprotein (rEgp) expressed by baculovirus using a column of G100 Sephadex.

SUPEROSE 6 CHROMATOGAPHY

Figure 3. Chromatographic analysis of recombinant dengue 2 envelope glycoprotein (rEgp) expressed by baculovirus using fast pressure liquid chromatography (FPLC) and a column of Superose 6.

Figure 4. Effect of sarkosyl on chromatographic elution profile of recombinant dengue 2 envelope glycoprotein (rEgp) analyzed using a Superose 6 column and fast pressure liquid chromatography.

Figure 5. Effect of sonication on chromatographic elution profile of recombinant dengue 2 envelope glycoprotein (rEgp) analyzed using a Superose 6 column and fast pressure liquid chromatography.

Figure 6. Sucrose gradient centrifugation distribution of recombinant dengue 2 envelope glycoprotein (rEgp).

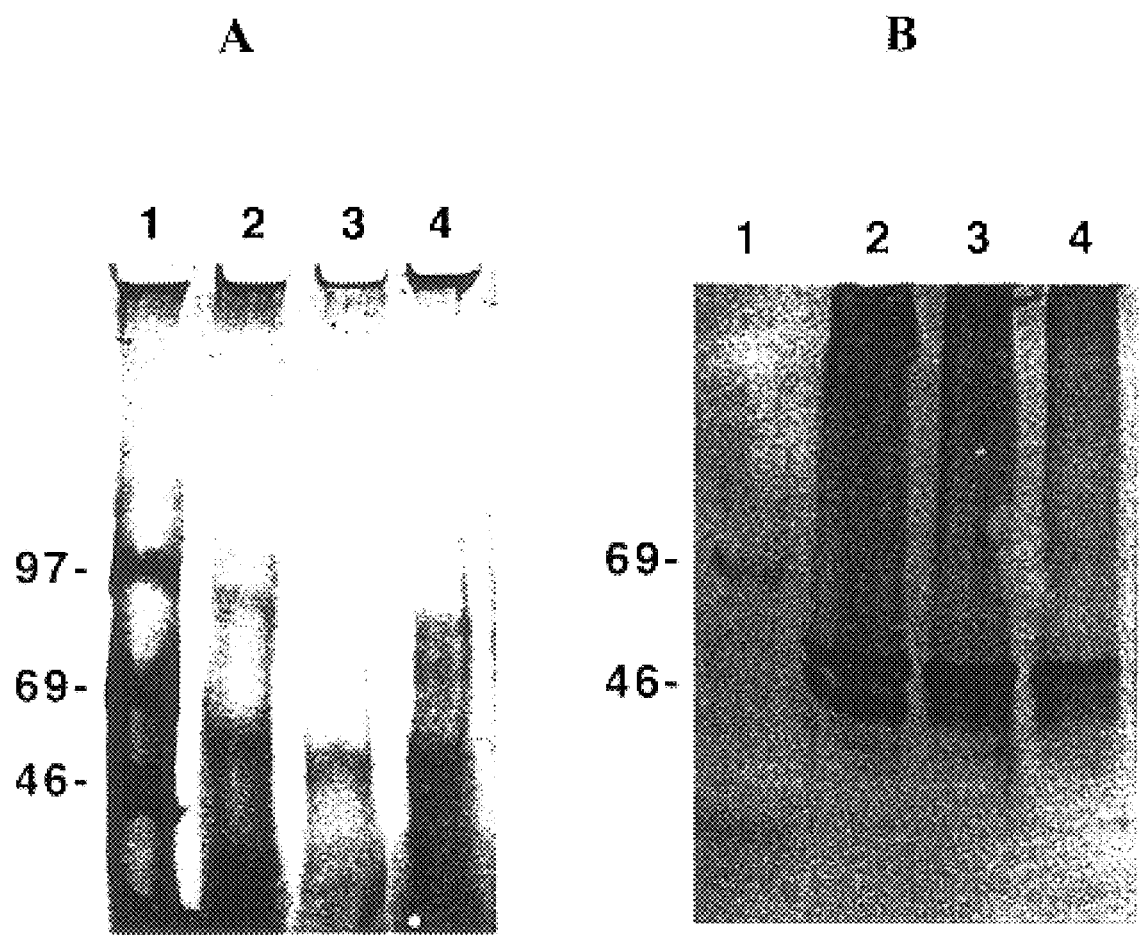
Figure 7 Polyacrylamide gel electrophoresis and immunoblot analysis of baculovirus-expressed dengue 2 recombinant envelope glycoprotein (rEgp)

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 1578 base pairs
       (B) TYPE: Nucleic acid
       (C) STRANDEDNESS: Single
       (D) TOPOLOGY: Linear (ii) SEQUENCE DESCRIPTION: SEQ ID NO:1:

```
ATGGCCGCAA TCCTGGCATA CACCATAGGA ACGACGCATT TCCAAAGAGT CCTGATATTC      60
ATCCTACTGA CAGCCATCGC TCCTTCAATG ACAATGCGCT GCATAGGAAT ATCAAATA       120
GACTTTGTGG AAGGAGTGTC AGGAGGGAGT TGGGTTGACA TAGTTTTAGA ACATGGAAG      180
TGTGTGACGA CGATGGCAAA AAATAAACCA ACACTGGACT TTGAACTGAT AAAAACAGA      240
GCCAAACAAC CCGCCACCTT AAGGAAGTAC TGTATAGAGG CTAAACTGAC CAACACGAC      300
ACAGACTCGC GCTGCCCAAC ACAAGGGGAA CCCACCCTGA TGAAGAGCA GGACAAAAG       360
TTTGTCTGCA AACATTCCAT GGTAGACAGA GGATGGGGAA ATGGATGTGG ATTATTTGG      420
AAAGGAGGCA TCGTGACCTG TGCCATGTTC ACATGCAAAA AGAACATGGA GGGAAAAAT     480
GTGCAGCCAG AAAACCTGGA ATACACTGTC GTTATAACAC CTCATTCAGG GGAAGAACA     540
GCAGTCGGAA ATGACACAGG AAAACATGGT AAAGAAGTCA AGATAACACC ACAGAGCTC     600
ATCACAGAGG CGGAACTGAC AGGCTATGGC ACTGTTACGA TGGAGTGCTC TCCAAGAAC     660
GGCCTCGACT TCAATGAGAT GGTGTTGCTG CAAATGAAAG ACAAAGCTTG GCTGGTGCA     720
AGACAATGGT TCCTAGACCT ACCGTTGCCA TGGCTGCCCG GAGCAGACAC ACAAGGATC     780
AATTGGATAC AGAAAGAGAC ACTGGTCACC TTCAAAAATC CCCATGCGAA AAAACAGGA     840
GTTGTTGTCT TAGGATCCCA AGAGGGGGCC ATGCATACAG CACTCACAGG GGCTACGGA     900
ATCCAGATGT CATCAGGAAA CCTGCTGTTC ACAGGACATC TTAAGTGCAG GCTGAGAAT     960
GACAAATTAC AACTTAAAGG GATGTCATAC TCCATGTGCA CAGGAAAGTT TAAAGTTG     1020
AAGGAAATAG CAGAAACACA ACATGGAACA ATAGTCATTA GAGTACAATA TGAAGGAG     1080
GGCTCTCCAT GCAAGACCCC TTTTGAGATA ATGGATCTGG AAAAAAGACA TGTTTTGG     1140
CGCCTGACCA CAGTCAACCC AATTGTAACA GAAAAGGACA GTCCAGTCAA CATAGAAG     1200
GAACCTCCAT TCGGAGACAG CTACATCATC ATAGGAGTGG AACCAGGACA ATTGAAGCT     1260
GACTGGTTCA AGAAAGGAAG TTCCATCGGC CAAATGTTTG AGACAACAAT GAGGGGAG     1320
AAAAGAATGG CCATTTTGGG CGACACAGCC TGGGATTTTG GATCTCTGGG AGGAGTGT     1380
ACATCAATAG GAAAGGCTCT CCACCAGGTT TTTGGAGCAA TCTACGGGGC TGCTTTCA     1440
GGGGTCTCAT GGACTATGAA GATCCTCATA GGAGTTATCA TCACATGGAT AGGAATGA     1500
TCACGTAGCA CATCACTGTC TGTGTCACTG GTATTAGTGG GAATCGTGAC ACTGTACT     1560
GGAGTTATGG TGCAGGCC                                                 1578
```

(2) INFORMATION FOR SEQ ID NO:2:

(i) SEQUENCE CHARACTERISTICS:
       (A) LENGTH: 526 amino acids
       (B) TYPE: amino acid
       (C) TOPOLOGY: Linear (ii) SEQUENCE DESCRIPTION: SEQ ID NO: 2:

```
Met Ala Ala Ile Leu Ala Tyr Thr Ile Gly Thr Thr His Phe Gly Arg
 1               5                  10                  15

Val Leu Ile Phe Ile Leu Leu Thr Ala Ile Ala Pro Ser Met Thr Met
            20                  25                  30

Arg Cys Ile Gly Ile Ser Asn Arg Asp Phe Val Glu Gly Tyr Ser Gly
        35                  40                  45

Gly Ser Trp Val Asp Ile Tyr Leu Glu His Gly Ser Cys Val Thr Thr
    50                  55                  60

Met Ala Lys Asn Lys Pro Thr Leu Asp Phe Glu Leu Ile Lys Thr Glu
65                  70                  75                  80

Ala Lys Gln Pro Ala Thr Leu Arg Lys Tyr Cys Ile Glu Ala Lys Leu
                85                  90                  95

Thr Asn Thr Thr Thr Asp Ser Arg Cys Pro Thr Gln Gly Glu Pro Thr
            100                 105                 110

Leu Asn Glu Glu Gln Asp Lys Arg Phe Val Cys Lys His Ser Met Val
        115                 120                 125

Asp Arg Gly Trp Gly Asn Gly Cys Gly Leu Phe Gly Lys Gly Gly Ile
    130                 135                 140

Val Thr Cys Ala Met Phe Thr Cys Lys Lys Asn Met Glu Gly Lys Ile
145                 150                 155                 160

Val Gln Pro Glu Asn Leu Glu Tyr Thr Val Ile Thr Pro His Ser
                165                 170                 175

Gly Glu Glu His Ala Val Gly Asn Gln Thr Gly Lys His Gln Lys Glu
            180                 185                 190

Val Lys Ile Thr Pro Gln Ser Ser Ile Thr Glu Ala Glu Leu Thr Gly
        195                 200                 205

Tyr Gly Thr Val Thr Met Glu Cys Ser Pro Arg Thr Gly Leu Asp Phe
    210                 215                 220

Asn Glu Met Val Leu Leu Asp Met Lys Asp Lys Ala Trp Leu Tyr His
225                 230                 235                 240

Arg Gln Trp Phe Leu Asp Leu Pro Leu Pro Trp Leu Pro Gly Ala Asp
                245                 250                 255

Thr Gln Gly Ser Asn Trp Ile Gln Lys Glu Thr Leu Val Thr Phe Lys
            260                 265                 270

Asn Pro His Ala Lys Lys Gln Asp Val Val Val Leu Gly Ser Gln Glu
        275                 280                 285

Gly Ala Met His Thr Ala Leu Thr Gly Ala Thr Glu Ile Gln Met Ser
    290                 295                 300

Ser Gly Asn Leu Leu Phe Thr Gly His Leu Lys Cys Arg Leu Arg Met
305                 310                 315                 320

Asp Lys Leu Gln Leu Lys Gly Met Ser Tyr Ser Met Cys Thr Gly Lys
                325                 330                 335

Phe Lys Val Val Lys Glu Ile Ala Glu Thr Gln His Gly Thr Ile Val
            340                 345                 350

Ile Arg Val Gln Tyr Glu Gly Asp Gly Ser Pro Cys Lys Thr Pro Phe
        355                 360                 365

Glu Ile Met Asp Leu Glu Lys Arg His Val Leu Gly Arg Leu Thr Thr
    370                 375                 380

Val Asn Pro Ile Val Thr Glu Lys Asp Ser Pro Val Asn Ile Glu Ala
385                 390                 395                 400

Glu Pro Pro Phe Gly Gln Ser Tyr Ile Ile Ile Gly Val Glu Pro Gly
```

```
                    405                    410                    415
Gln Leu Lys Leu Asp Trp Phe Lys Lys Gly Ser Ser Ile Gly Gln Met
            420                    425                430

Phe Glu Thr Thr Met Arg Gly Ala Lys Arg Met Ala Ile Leu Gly Asp
        435                    440                445

Thr Ala Trp Asp Phe Gly Ser Lys Gly Gly Val Phe Thr Ser Ile Gly
    450                    455                460

Lys Ala Lys His Gln Val Phe Gly Ala Ile Tyr Gly Ala Ala Phe Ser
465                     470                 475                 480

Gly Val Ser Trp Thr Met Lys Ile Leu Ile Gly Val Ile Ile Thr Trp
                485                    490                495

Ile Gly Met Asn Ser Arg Ser Thr Ser Leu Ser Val Ser Leu Val Leu
            500                    505                510

Val Gly Ile Val Thr Leu Tyr Leu Gly Val Met Val Gln Ala
        515                    520                525

(2) INFORMATION FOR SEQ ID NO: 3:

(i) SEQUENCE CHARACTERISTICS:
        (A) LENGTH:  31 base pairs
        (B) TYPE:  Nucleic Acid
        (C) STRANDEDNESS: Double
        (D) TOPOLOGY: Linear (ii) SEQUENCE DESCRIPTION: SEQ ID NO: 3:

ACTGAGATCT  ATGATGGCCG  CAATCCTGGC  A                                    31

(2) INFORMATION FOR SEQ ID NO: 4:

(i) SEQUENCE CHARACTERISTICS:
        (A) LENGTH: 31 base pairs
        (B) TYPE:  Nucleic Acid
        (C) STRANDEDNESS: Double
        (D) TOPOLOGY: Linear (ii) SEQUENCE DESCRIPTION: SEQ ID NO: 4:

CTGACTGCAG  TTACGGCCTG  CACCATAACT  C                                    31
```

RECOMBINANT DENGUE VIRUS DNA FRAGMENT

INTRODUCTION

This invention relates to the production and purification of a recombinant protein for use as a diagnostic tool and as a vaccine against Dengue virus.

Dengue (DEN) viruses are human pathogens with a significant threat to world health. These viruses are estimated to cause several hundred thousand cases of dengue fever, dengue hemorrhagic fever (DHF) and dengue shock syndrome (DSS) annually (Shope, R. E. In: *The Togaviruses*. Schlesinger, R. W. (Ed.) Academic Press, New York. 1980, pp. 47–82; Monath, T. P. In: *The Togaviridae and Flaviviridae*, Schlesinger, S. and Schlesinger, M. J. (Eds.) New York and London, 1986, pp. 375–440; Halstead, S. B. *Bull. W.H.O.* 1980, 58, 1–21; Halstead, S. B. *Am. J. Epidemiol.* 1984, 114, 632–648) The complete content of all documents cited herein are hereby incorporated by reference. Dengue viruses are members of the family Flaviridae and are transmitted by Aedes mosquitoes (Halstead, S. B. *Science* 1988, 239, 476–481). There are four serological types, DEN-1, DEN-2, DEN-3 and DEN-4, distinguishable by complement-fixation assays (Sabin, A. B. and Young, I. A. *Proc. Soci. Exp. Biol. Med.* 1949, 69, 291–296), virus plaque-reduction neutralization tests (Russell, P. K. and Nisalak, A. *J. Immunol.* 1967, 99, 291–296) and immunoassays using monoclonal antibodies (MAbs) (Gentry, M. K. et al. *Am. J. Trop. Med. Hyg.* 1982, 31, 548–555; Henchal, E. A. et al. *Am. J. Trop. Med. Hyg.* 1982, 31, 830–836).

Dengue viruses are composed of a single-stranded RNA molecule of positive polarity (messenger sense) which is contained within a nucleocapsid composed of capsid (C) protein. The capsid is surrounded by a lipid envelope about 50 nm in diameter in which are embedded the envelope (E) glycoprotein and the matrix (M) protein. Both the structural and nonstructural (NS) proteins are encoded by a single, long open reading frame of about 10.5 kilobases arranged as follows: C-PreM/M-E-NS1-NS2A-NS2B-NS3-NS4A-NS5 (Rice, C. M. et al. *Science* 1985, 229, 726–733; Wengler, G. et al. *Virology* 1985, 147, 264–274; Castle, E. et al. *Virology* 1986, 149, 10–26; Zhao, B. et al. *Virology* 1986, 155, 77–88; Mason, P. W. et al. *Virology* 1987, 161, 262–267; Mackow, E. et al. *Virology* 1987, 159, 217–228; Sumiyoshi, H. et al. *Virology* 1987, 161, 497–510; Irie, K. et al. *Gene* 1989, 74, 197–211).

Attempts to prevent DEN virus infection have focused on the production of a vaccine which would protect against all four serotypes. However, despite more than 50 years of effort, safe and effective dengue virus vaccines have not been developed. Candidate vaccines currently being tested fall into two categories: live attenuated dengue virus vaccines and subunit vaccines, each with its own drawbacks.

Live attenuated virus vaccines have been demonstrated to be either under-attenuated (cause disease) or over-attenuated (fail to immunize). Even an optimally-attenuated live virus vaccine can revert to a virulent (disease-causing) form through mutation. Live dengue viruses are also sensitive to heat, making it difficult and costly to maintain the vaccine in some tropical and subtropical countries where the vaccine may be needed most.

Recombinant subunit vaccines have the advantage of eliminating the risk of infectivity and greater chemical stability. However, the subunit vaccines of flavivirus structural and NS proteins produced in expression vectors including baculovirus, vaccinia virus and *E. coli* reported so far elicit only low titers of neutralizing antibody and are difficult to produce in large quantities and pure form (Putnak, J. R. et al. *Virology* 1988, 163, 93–103; Putnak, J. R. et al. *Am. J. Trop. Med. Hyg.* 1991, 45, 159–167; Zhang, Y. M. et al. *J. Virol.* 1988, 62, 3027–3031; Lai, C. J. et al. In: *Vaccines, Modern Approaches to New Vaccines Including Prevention of AIDS* (Eds. Lerner, R. A. et al.), Cold Spring Harbor Laboratory Press, New York, 89, 1989, pp. 351–356; Bray, M. et al. *J. Virol.* 1989, 63, 2853–2856; Bray, M. and Lai, C. J. *Virology* 1991, 185, 505–508; Men, R. et al. *J. Virol.* 1991, 65, 1400–1407; Mason, P. W. et al. *Virology* 1987, 158, 361–372; Mason, P. W. et al. *J. Gen. Virol.* 1989, 70, 2037–2049; Mason, P. W. et al. *J. Gen. Virol* 1990, 71, 2107–2114; Murray, J. M. et al. *J. Gen. Virol,* 1993, 74, 175–182; Preugschat, F. et al. *J. Virol* 1990, 64, 4364–4374).

Both the envelope (E) and the nonstructural protein 1 (NS1) are candidates for recombinant, subunit vaccines against DEN virus. The E glycoprotein is the major surface protein of the virion. It functions in virion attachment to host cells and it can be detected by its ability to hemagglutinate goose erythrocytes. As an antigen, it contains virus-neutralizing epitopes (Stevens, T. M. et al. *Virology* 1965, 27, 103–112; Smith, T. J. et al. *J. Virol* 1970, 5, 524–532; Rice, C. M. and Strauss, J. H. *J. Mol. Biol.* 1982, 154, 325–348; Brinton, M. A. In: *Togaviridae and Flaviridae*. Schlesinger, S. and M. J. Schlesinger (Eds.), M. J. Plenum, New York, 1986, pp. 327–365; Heinz, F. X. *Adv. Virus Res.* 1986, 31, 103–168; Westaway, E. G. *Adv. Virus Res.* 1987, 33, 45–90; Hahn, Y. S. et al. *Arch. Virol.* 1990, 115, 251–265). Neutralizing antibodies, believed to correlate with protection, and hemagglutination-inhibiting (HI) antibodies develop following natural infection. Mice immunized with purified DEN-2 E antigen develop neutralizing antibodies and are protected against lethal virus challenge (Feighny, R. J. et al. *Am. J. Trop. Med. Hyg.* 1992, 47, 405–412).

Recombinant DEN proteins have been produced using the baculovirus system for the purpose of developing a vaccine. Results have been variable and sometimes disappointing. Several strategies have been used to produce the DEN E protein in the baculovirus system. One strategy used a truncated gene to produce the E protein without the hydrophobic transmembrane segment of the carboxy terminus. The purpose of this approach was to promote secretion and solubility of the protein. Proteins produced in this manner were minimally immunogenic in mice (Putnak, R. et al. *Am. J. Trop. Med. Hyg.,* 1993, 45: 159–167; Zhang, Y. M. et al., *J. Virol.,* 1988, 62: 3027–3031). Another strategy used a polygene that encoded the capsid, premembrane and two nonstructural proteins, C-prM-E-NS1-NS2 (Delenda et al. *J. Gen. Virol,* 1994, 75: 1569–1578). This construct produced the full length E protein by cleavage of the polyprotein. Neutralizing antibody to the full length E protein was not elicited by that product although protection was induced. The complex nature of the construct precludes an analysis of the reason for protection in the absence of neutralizing antibody but the presence of NS1 in the construct was speculated to have induced the protective response. Another strategy employed a construct that contained a polygene encoding C, preM and a truncated E protein (Deubel et al. *Virology,* 1991, 180: 442–447). Although the truncated E reacted with some E-specific monoclonal antibodies (mAbs), reactivity was weaker than that obtained with native virus.

Therefore, in view of the problems with the presently available vaccines discussed above, there is a need for a DEN vaccine that elicits very high titers of neutralizing antibody, provides protection against the disease, has no possibility of infectivity to the immunized host, can be produced easily in pure form, and is chemically stable.

SUMMARY

The present invention is directed to a subunit vaccine that satisfies this need. The recombinant DEN virus subunit vaccine of the present invention comprises the full dengue virus envelope protein, expressed in baculovirus and capable of self-assembling into a particle. Dengue envelope protein has been expressed in the baculovirus system by others. The previously produced products were poorly immunogenic when tested in animals. None of the previously made products are known to form particles. The protein is expressed and purified as a particle composed of multiple dengue envelope protein molecules. Particles are more immunogenic than soluble proteins, possibly because they can crosslink cell surface immunoglobulins on B cells. The envelope protein particle of the present invention is produced in baculovirus in large quantities and in pure form, elicits high titers of neutralizing antibody and is protective against the disease in the immunized animal.

The present invention describes the production of the DEN envelope protein particle by cloning the complementary DNA (cDNA) sequences encoding the envelope protein fragment into an expression vector such that the recombinant dengue protein can be expressed. The recombinant protein is produced in baculovirus, isolated and purified as a particle which is antigenic, reactive with dengue virus-specific and monoclonal antibodies and capable of eliciting the production of neutralizing antibodies when inoculated into mice. The administration of this recombinant subunit vaccine is demonstrated to protect mice, an accepted animal model, against morbidity and mortality following challenge with live dengue virus.

Therefore, it is an object of the present invention to provide a DEN 2 cDNA fragment encoding the full envelope glycoprotein, said gene containing 1485 nucleotides plus 93 adjacent upstream sequences and extending from 844 to 2422 of the viral genome and is useful as a diagnostic agent and a naked DNA vaccine.

It is another object of the invention to provide a recombinant vector designed to produce the recombinant DEN envelope protein for use as a vaccine and as a diagnostic agent.

It is still another object of the invention to provide a purified DEN envelope protein particle useful as a vaccine against DEN disease and for detecting the presence of said disease in a suspected patient.

It is another object of the present invention to provide a method for the purification of recombinant DEN envelope protein particle for use as a vaccine or as a diagnostic tool.

It is yet another object of the invention to provide a DEN virus vaccine effective for the production of antigenic and immunogenic response resulting in the protection of an animal against dengue virus disease.

BRIEF DESCRIPTION OF THE DRAWINGS

These and other features, aspects, and advantages of the present invention will become better understood with reference to the following description and appended claims, and accompanying drawings where:

FIGS. 1. (A–C) Illustration of the pBlueBacIII shuttle vector and gene sequences used for expression of the dengue 2 virus envelope glycoprotein in insect cells. A) illustration of relative positions of dengue 2 virus structural protein genes capsid ©, premembrane (prM) and envelope (E), and the N-terminal end of the adjacent non-structural protein NS1; B) nucleotide coordinates of the E gene construct used for insertion into shuttle vector pBluBacIII, extending from nucleotides 844 to 2422, including a sequence from vector identifying relative positions of the beta-galactosidase gene (lacZ), polydedrin promoter (Pph), BglII/PstI cloning site, recombination sequences and ampicillin resistance gene (amp).

FIG. 2. Gel filtration of dengue 2 virus recombinant envelope glycoprotein (rEgp) expressed by baculovirus using a column of G100 Sephadex. The column was equilibrated in phosphate buffered saline (PBS) and fractions were eluted in PBS. Fractions were assayed for antigenic reactivity using the antigen dot blot assay and hyperimmune murine ascites fluid specific for dengue 2 virus. Data are plotted as absorbance at 280 nanometers (A260 nm) and counts per minute veses fraction number. Solid line represents relative absorbance of the sample at 280 nm; dashed line represents antigenic activity; dotted line represents the elution pattern of column calibration standards thyroglobulin, 670 kilodaltons (kD), bovine gamma globulin, 158 kD, chicken ovalbumin, 44 kD and myoglobin, 17 kD.

FIGS. 3. (A–B) Chromatographic analysis of recombinant dengue 2 virus envelope glycoprotein (rEgp) expressed by baculovirus using fast pressure liquid chromatography (FPLC) and a Superose 6 column. The column was equilibrated with phosphate buffered saline (PBS) and protein was eluted with the same. A. Column fractions were assayed for antigen using anti-dengue 2 hyperimmune ascited fluid in a dot blot assay. Data are plotted as absorbance at 280 nanometers (A260 nm) and counts per minute (y axis) vesus fraction number. B. The column as calibrated with molecular weights standards thyroglobulin, 670 kilodaltons (kD), bovine gamma globulin, 158 kD, chicken ovalbumin, 44 kD and myoglobin, 17 kD.

FIGS. 4. (A–D) Effect of sarkosyl on chromatographic elution profile of recombinant dengue 2 virus envelope glycoprotein (rEgp) analyzed using a Superose 6 column and fast pressure liquid chromatography (FPLC). The column was equilibrated in phosphate buffered saline (PBS) containing 0.1% sodium sarkosyl and protein containing recombinant dengue 2 envelope glycoprotein was eluted in PBS containing: A) 0.1% sarkosyl, B) 1.0% sarkosyl, C) 20% sarkosyl and D) 3.0% sarkosyl. Column fractions were assayed for antigenic activity using anti-dengue 2 hyperimmune ascites fluid in a dot blot assay. Data are plotted as absorbance (solid line) at 280 nanometers (A260) and counts per minute (dotted line) vesus fraction.

FIGS. 5. (A–C) Effect of sonication on chromatographic elution profile of recombinant dengue 2 virus envelope glycoprotein (rEgp) analyzed usisng a Superose 6 column and fast pressure liquid chromatography (FPLC). Insect cells (Trichoplusia ni) infected with recombinant baculovirus expressing the dengue 2 virus envelope glycoprotein were sonicated in phosphate buffered saline (PBS) for 0, 20 and 30 minutes and eluted from a Superose 6 column by fast pressure liquid chromatography (FPLC). Solid line represents relative amounts of protein detected by absorbancy at 280 nanometers (A260) and dotted line (counts per minute) represents antigenic reactivity of fraction aliquots with anti-dengue 2 hyperimmune ascites fluid in a dot blot assay.

FIG. 6. Sucrose gradient centrifugation distribution of recombinant dengue 2 virus envelope glycoprotein (rEgp).

Insect cells (Spodoptera frugiperda) infected with recombinant baculovirus were pelleted at low speed and protein remaining in the supernatant was pelleted at 100,000 x g for 2.5 hours. The resulting microsomal pellet was subjected to density gradient ultracentrifugation at 100,000 x g for 2.5 hours using a stp gradient of 5–30% sucrose in phosphate buffered saline (PBS). Fractions were assayed for antigenic activity (shaded area) using anti-dengue 2 hyperimmune ascites fluid in a dot blot assay.

FIGS. 7. (A–B) Polyacrylamide gelelectrophoresis and immunoblot analysis of baculovirus-expressed dengue 2 virus recombinant envelope glycoprotein (rEgp). The micorsomal pellet (described, FIG. 6) was ultracentrifuged through a cushion of 30% sucrose in phosphate buffered saline (PBS) for 2.5 hours at 100,000 x g. Proteins in the microsomal pellet or 30% sucrose pellet were resuspended in PBS, sonicated briefly and bolied in SDS sample buffer for 5 minutes before electrophoresis on a 10% SDS polyacrylamide gel. A) Coomassie-blue stained gel: lane 1, molecular weight standard; lane 2, microsomal pellet; lanes 3 and 4, 30% sucrose pellets (contained in 10 or 20 microliters respectively). B) Proteins were electrophoretically transferred to nitrocellulose paper and this immunoblot was probed with hyperimmune mouse ascites fluid specific for dengue 2 virus. Lanes in B correspond to lanes in A.

DETAILED DESCRIPTION

In one embodiment, the present invention relates to a DNA or cDNA segment which encodes the complete E protein of DEN-2 and the carboxy terminus of membrane/premembrane protein extending from nucleotide 844 to 2422 of the DEN-2 viral genome and including linear and conformational, neutralizing epitopes said sequence identified as SEQ ID NO: 1.

DNA sequences to which the invention also relates include sequences which encode the specific protein epitopes within said sequence which elicit neutralizing antibody production in animals upon administration of the protein encoded by said DNA sequences. Specifically, such sequences include regions encoding neutralizing epitopes present on the nucleotide sequence encompassing amino acids 1 through 495 of the E protein several of which have been mapped (Henchel, E. et al. *Am. J. Trop. Med. Hyg.*, 1985, 34: 162–167) and found to be conformational as well as linear epitopes examples of which are found in TABLE 1 under Results section.

In another embodiment, the present invention relates to a recombinant DNA molecule that includes a vector and a DNA sequence as described above (advantageously, a DNA sequence encoding the protein having the neutralizing antibody-eliciting characteristics of that protein). The vector can take the form of a virus shuttle vector such as, for example, baculovirus vectors pBlueBac-III, pBlueBac-HIS-A-B-C, MaxBac; a plasmid, or eukaryotic expression vectors such as such as GST gene fusion vectors, pGEx-3x, pGEx-2T, pGEx, mammalian cell vectors (pMSG, pMAMneo) or vectors for expression in drosophila or yeast, in addition to other vectors known to people in the art. The DNA sequence can be present in the vector operably linked to regulatory elements, including, for example, a promoter or a highly purified human IgG molecule, for example Protein A, an adjuvant, a carrier, or an agent for aid in purification of the antigen as long as the rEgp is expressed as a particle. The recombinant molecule can be suitable for transforming transfecting eukaryotic cells for example, mammalian cells such as VERO or BHK cells, or insect cells such as Sf-9 (*Spodopter frugiperda*), C6/36 (*Aedes albopictus*), and Trichoplusia ni (High five) mosquito cells, Drosophila cells, and yeast (*Ssccharomyces cerevisiae*) among others.

In another embodiment, the present invention relates to a recombinant protein having an amino acid sequence corresponding to SEQ ID NO: 2 and encompassing 495 amino acids of the E protein and 31 amino acids of the carboxy-terminus of the adjacent M/prM protein from DEN-2 or any allelic variation thereof which maintains the neutralizing antibody production characteristic of the recombinant protein. As an example, the protein (or polypeptide) can have an amino acid sequence corresponding to an epitope such as a B-cell and T-cell epitope present on the envelope glycoprotein of DEN-2, or conformational epitopes examples of which are found in TABLE 1. In addition, the protein or polypeptide, or a portion thereof, can be fused to other proteins or polypeptides which increase its antigenicity, thereby producing higher titers of neutralizing antibody when used as a vaccine. Examples of such proteins or polypeptides include any adjuvants or carriers safe for human use, such as aluminum hydroxide and liposomes.

In yet another embodiment, the present invention relates to a recombinant protein as described above which is capable of assembling into more than one protein unit. Assembly of the individual protein units can be by hydrophobic forces, or chemical forces, by cross-linking reagents, or the assembled protein can be further stabilized by cross-linking reagents, and liposomes. The particle can encompass from at least 2 units of envelope protein. Such a particle can provide higher immunogenicity and possibly cross-link cell surface immunoglobulins on B cells.

In a further embodiment, the present invention relates to host cells stably transformed or transfected with the above-described recombinant DNA constructs. The host cell can be lower eukaryotic (for example, yeast or insect) or higher eukaryotic (for example, all mammals, including but not limited to mouse and human). For instance, transient or stable transfections can be accomplished into CHO or Vero cells. Transformation or transfection can be accomplished using protocols and materials well known in the art. The transformed or transfected host cells can be used as a source of the DNA sequences described above. When the recombinant molecule takes the form of an expression system, the transformed or transfected cells can be used as a source of the above-described recombinant protein.

In a further embodiment, the present invention relates to a method of producing the recombinant protein which includes culturing the above-described host cells, under conditions such that the DNA fragment is expressed and the recombinant protein is produced thereby. The recombinant protein can then be isolated using methodology well known in the art. The recombinant protein can be used as a vaccine for immunity against infection with flaviviruses or as a diagnostic tool for detection of viral infection.

In yet another embodiment, the present invention relates to a method of purifying the recombinant protein particles, said method comprising the steps of:
 (i) harvesting cells expressing recombinant DEN envelope glycoprotein;
 (ii) separating a cell pellet and a supernatant from said harvested cells;
 (iii) lysing said cell pellet of step (ii) to release recombinant envelope glycoprotein;
 (iv) pelleting said recombinant envelope glycoprotein from said lysed cells;

(v) fractionating said recombinant envelope glycoprotein from steps (ii) and (v) through a density gradient;

(vi) collecting purified recombinant envelope glycoprotein from pellet.

The density gradient of step (vi) may be made of any density separation material such as cesium chloride, ficoll, or molecular sieve material. The recombinant envelope glycoprotein can also be pelleted from said supernatant. If desired, the cell debris can be pelleted or separated from said recombinant envelope glycoprotein after lysing cell pellet as described in (iii).

In a further embodiment, the present invention relates to a method of detecting the presence of DEN virus disease or antibodies against DEN virus in a sample. Using standard methodology well known in the art, a diagnostic assay can be constructed by coating on a surface (i.e. a solid support) for example, a microtitration plate or a membrane (e.g. nitrocellulose membrane), all or a unique portion of the recombinant envelope protein particle described above, and contacting it with the serum of a person suspected of having DEN fever. The presence of a resulting complex formed between the recombinant protein and antibodies specific therefor in the serum can be detected by any of the known methods common in the art, such as fluorescent antibody spectroscopy or colorimetry. This method of detection can be used, for example, for the diagnosis of DEN disease. This method when employing distinct rEgp particles specific for each DEN serotype, will allow the detection of the presence of each respective DEN serotype in a sample. Infection with more than one serotype is thought to play a role in the etiology of DEN haemorrhagic fever and DEN shock syndrome.

In addition, the present invention is related to a method of detecting flavivirus disease or antibodies against flavivirus in a sample. Dengue viruses are members of the family Flaviridae which includes over sixty members among which there is considerable genetic and antigenic similarity but no significant cross-neutralization. It would be apparent to persons in the art to apply the concepts of the present invention exemplified in DEN-2 to similar proteins and DNA sequences present in other related flaviviruses such as yellow fever, Japanese encephalitis and tick-borne encephalitis viruses.

In another embodiment, the present invention relates to a diagnostic kit which contains the recombinant envelope protein particle and ancillary reagents that are well known in the art and that are suitable for use in detecting the presence of antibodies to flavivirus antigens in serum or a tissue sample, specifically antibodies to DEN virus. Tissue samples contemplated can be monkey and human, or other mammals.

In another embodiment, the present invention relates to a vaccine for protection against a flavivirus disease. The vaccine can be prepared by inducing expression of the recombinant expression vector described above in either a higher mammalian or lower (insect, yeast, fungi) eukaryotic host and purifying the recombinant glycoprotein particle described above. The purified particles are prepared for administration to mammals by methods known in the art, which can include preparing the particle under sterile conditions and adding an adjuvant. The vaccine can be lyophilized to produce a flavivirus vaccine in a dried form for ease in transportation and storage. Further, the vaccine may be prepared in the form of a mixed vaccine which contains the recombinant protein described above and at least one other antigen as long as the added antigen does not interfere with the effectiveness of the dengue vaccine and the side effects and adverse reactions are not increased additively or synergistically. It is envisioned that a tetravalent vaccine composed of recombinant antigenic proteins from the four serotypes of dengue virus, DEN-1, DEN-2, DEN-3, and DEN-4 can be produced to provide protection against dengue disease.

The vaccine may be stored in a sealed vial, ampoule or the like. The present vaccine can generally be administered in the form of a liquid or suspension. In the case where the vaccine is in a dried form, the vaccine is dissolved or suspended in sterilized distilled water before administration. Generally, the vaccine may be administered subcutaneously, intradermally or intramuscularly in a dose effective for the production of neutralizing antibody and protection from infection.

In another embodiment, the present invention relates to a naked DNA or RNA vaccine. The DEN DNA fragment, of the present invention described in SEQ ID NO: 1 or a portion thereof, or an allelic form thereof, can be administered as a vaccine to protect against DEN virus disease and to elicit neutralizing antibodies against the virus. The DNA can be converted to RNA for example by subcloning the said DNA into a transcriptional vector, such as pGEM family of plasmid vectors, or under control of a transcriptional promoter of a virus such as vaccinia, and the RNA used as a naked RNA vaccine. It is understood and apparent to a person with ordinary skill in the art that due to the similarity between different serotypes of DEN as well as similarities between flaviviruses, a DNA sequence from any DEN serotype or flavivirus encoding the complete envelope protein of its respective flavivirus can be used as a naked DNA vaccine against infection with its respective virus. The DEN-2 naked DNA or RNA vaccine can be injected alone, or combined with at least one other antigen or DNA or RNA fragment as long as the added antigen or DNA or RNA fragment does not interfere with the effectiveness of the DEN vaccine and the side effects and adverse reactions are not increased additively or synergistically. It is envisioned that a tetravalent vaccine composed of DNA or RNA fragments from the four serotypes of dengue virus, DEN-1, DEN-2, DEN-3, and DEN-4 can be produced to provide protection against dengue disease.

The naked DNA or RNA vaccine of the present invention can be administered for example intermuscularly, or alternatively, can be used in nose drops. The DNA or RNA fragment or a portion thereof can be injected as naked DNA or RNA, as DNA or RNA encapsulated in liposomes, as DNA or RNA entrapped in proteoliposomes containing viral envelope receptor proteins (Nicolau, C. et al. *Proc. Natl. Acad. Sci. U.S.A.* 1983, 80, 1068; Kanoda, Y., et al. *Science* 1989, 243, 375; Mannino, R. J. et al. *Biotechniques* 1988, 6, 682). Alternatively, the DNA can be injected along with a carrier. A carrier can be a protein or such as a cytokine, for example interleukin 2, or a polylysine-glycoprotein carrier (Wu, G. Y. and Wu, C. H. *J. Biol. Chem.* 1988, 263, 14621), or a nonreplicating vector, for example expression vectors containing either the Rous sarcoma virus or cytomegalovirus promoters. Such carrier proteins and vectors and methods for using same are known to a person in the art (See for example, Acsadi, G. et al. *Nature* 1991, 352, 815–818). In addition, the DNA or RNA could be coated onto tiny gold beads and said beads introduced into the skin with, for example, a gene gun (Cohen, J. *Science* 1993, 259, 1691–1692; Ulmer, J. B. et al. *Science* 1993, 259, 1745–1749).

Described below are examples of the present invention which are provided only for illustrative purposes, and not to limit the scope of the present invention. In light of the present disclosure, numerous embodiment within the scope of the claims will be apparent to those of ordinary skill in the art.

The following MATERIALS AND METHODS were used in the examples that follow.

Cells and viruses. Dengue-2 virus was propagated in *Aedes albopictus* cells (C6/36 cells, American Type Tissue Culture Collection, ATCC, Rockville, Md.). To propagate virus, C6/36 cells were grown at 28° C. in $CO_2$-independent medium (Gibco, Grand Island, N.Y.) containing 10% fetal bovine serum (FBS, heat inactivated at 56° C. for 30 min, Sigma, St Louis, Mo.). Wild-type DEN-2 virus (strain PR 159) was the source of genomic RNA for synthesis of the rEgp gene. A mouse-adapted New Guinea C strain was used for immunizations and plaque neutralization assays. African green monkey kidney cells were purchased from ATCC. Baculovirus (*Autographa californica* nuclear polyhedrosis virus, AcPNV, Invitrogen, San Diego, Calif.) was propagated in *Spodoptera frugiperda* (Sf-9 and Sf-21) and Trichoplusia ni (High five) cells (Invitrogen). High five cells and Sf-9 cells were cultured in tissue culture flasks at 28° C. in TNMFH medium (Biowhittaker, Walkersville, Md.) supplemented with 10% FBS, penicillin (100 units U/ml), streptomycin (100 μg/ml), glutamine (2 mM) and gentamycin (50 mg/ml). Recombinant baculoviruses were isolated in Sf-9 cells following previously described procedures (5). The Sf-21 cells were grown in 10 liter spinner culture in TNMFH media supplemented as above for High five and Sf-9 cells.

Cloning of the DEN-2 envelope gene. The gene encoding the DEN-2 Egp and an adjacent upstream translocation signal sequence (Markoff, L., *J. Virol.,* 1989, 63:3345–3352) was derived by reverse transcription of viral genomic RNA followed by amplification of cDNA by the polymerase chain reaction. Dengue-2 virus RNA was purified from supernatants of virus-infected C6/36 cells by guanidine isothiocyanatephenol chloroform:isoamyl alcohol extraction (Chomczynski and Sacchi, *Anal Biochem.,* 1987, 162:156–159). Primers were constructed that incorporated enzyme restriction sequences onto ends of the Egp gene fragment, and the fragment was inserted into the baculovirus transfer vector pBlueBacIII (Invitrogen). The sequence of the recombinant Egp (rEgp) gene fragment in pBlueBacIII was determined to be identical to that of the native Egp gene (Hahn, et al. *Virology,* 1988, 185:401–410) by dideoxy sequencing (Sanger et al., *Proc. Nail. Acad. Sci. U.S.A.,* 1977, 74: 5463–5467).

Cotransfection and purification of recombinant baculoviruses. Recombinant baculoviruses were generated by co-transfecting Sf-9 cells with a recombinant pBlueBac III plasmid together with commercially-prepared linear baculovirus (Invitrogen, San Diego, Calif.). The Egp gene fragment was transferred into the baculovirus genome by homologous recombination (Summers and Smith, *A Manual of Methods for Baculovirus Vectors and Insect Cell Culture Procedure*. Texas Agricultural Experimental Station Bulletin No. 1555, Texas Agricultural Station, College Station, Tex., 1987). Plaque assays in Sf-9 cells were used to isolate the recombinant baculovirus clones which yielded blue plaques due to the transfer of the β-galactosidase gene from the pBlueBac III plasmid. Following infection of Sf-9 cells with a plaque purified recombinant baculovirus clone, DNA was extracted from cells and the presence of the Egp gene was confirmed by hybridization of a $^{32}P$-labeled Egp gene probe with the DNA.

SDS-polyacrylamide gel electrophoresis and western blotting. Proteins were resolved on a 10% SDS-polyacrylamide gel (Laemmli, U. K. *Nature,* 1970, 227:680–685). Samples were either boiled for 5 minutes or not boiled before application to the gel. Proteins were blotted onto nitrocellulose paper using a dry blot apparatus (Enprotech, Integrated Separation Systems, Hyde Park, Mass.) as recommended by the manufacturer. Following protein transfer, the nitrocellulose was blocked for 30 minutes in PBS-0.05% azide containing 5% powdered milk (blocking buffer) and incubated overnight in blocking buffer containing a 1:500 dilution of anti-DEN-2 hyperimmune mouse ascites fluid (HMAF, 11). The blot was washed 3 times in PBS containing 0.05% Tween 20 (PBS-T) and incubated for 1 hour in alkaline phosphatase-conjugated goat anti-mouse IgG (Kirkegaard and Perry, Gaithersburg, Md.). The blot was washed 3 times in PBS-T and finally in Tris-glycine-saline, (TGS), pH 8.0. Antigenic bands were visualized by incubating the blot in TGS containing 2 mg/ml napthol and 1 mg/ml phenol red (Sigma, St Louis, Mo.).

Antigen dot blot. Samples were applied to nitrocellulose paper using a 96-well manifold under vacuum. The paper was blocked and incubated overnight in blocking buffer containing HMAF diluted 1:500. The paper was washed 3 times with PBS-T and incubated for 1 hour in blocking buffer containing goat anti-mouse immunoglobulin gamma (Kirkegaard and Perry) labeled with $^{125}I$ (Gentry M. K. et al., *Am. J. Trop. Med. Hyg.,* 1982, 31: 548–555), using labeled antibody at $10^6$ cpm/ml of blocking buffer. Following incubation with the labeled antibody, the paper was washed 3 times with PBS-T, cut into sample squares and counted in a clinical gamma counter (Pharmacia-LKB, Piscataway, N.J.).

Antibody Affinity Assays. A particle fluorescence assay (PFCIA) was developed based on previous methodologies (Scatchard, G. *Ann. N.Y. Acad. Sci.,* 1989, 51:660–672; Schots et al. *Virology,* 1988, 162:167–180) to quantitate fluorescence in an antibody-antigen binding assay using FITC-labeled purified mAbs. The amount of fluorescence, via antibody, bound to antigen adsorbed to polystyrene beads was assayed using polycarbonate IDEXX assay plates (IDEXX, Westbrook, Me.) and a PFCIA analyzer (IDEXX). Binding affinities of the three mAbs were measured under neutral (pH 7.0) and acidic (pH 5.0) buffering conditions. Antigens tested in the assay were: rEgp derived from the cell lysate described above, partially purified rEgp obtained by column fractionation (see below) of the cell lysates, or DEN-2 virus (NGC strain). Antigen and serially-diluted FITC-conjugated Egp-specific mAbs (100 μg/ml) were separately adsorbed onto polystyrene beads (IDEXX) for 1 hour at room temperature. Protein-bound beads were washed twice in PBS and resuspended in PBS containing 0.1% bovine serum albumin (BSA) and 0.1% sodium azide at a final particle concentration of 0.25% w/v. The assay was conducted in triplicate for each mAb dilution. For the assay, blocking buffer (PBS containing 1% BSA) was distributed into wells of IDEXX plates followed by the addition of antigen-coated beads. Serial dilutions of FITC-labeled mAbs were then added to the wells and plates were incubated in the analyzer for washing (PBS, pH 7.2, 0.1% BSA and 0.02% Tween) and fluorescence quantitation. Results were analyzed by the Ligand software program, PJ Munson, Division of Computer Research and Technology, The National Institutes of Health, Bethesda, Md.

Gel Filtration Chromatography. Clarified supernatants of lysed, infected High five cells were strained through a 0.4 micron filter and fractionated by gravity flow using a column of Sephadex G-100 (1.5×30 cm) or by Fast Pressure Liquid Chromatography (Pharmacia) using columns of Sepharose-6 and Sepharose 12 (2.5×60 cm). Fractions were collected and aliquots of the fractions were assayed for antigenic activity by antigen dot blot assay.

Purification of rEgp by ultracentrifugation. Infected High five or Sf-21 cells were harvested, pelleted by low-speed centrifugation and washed several times with PBS. The pellet was disrupted by sonication and clarified by low-speed centrifugation. The supernatant was centrifuged at 100,000×g for 90 minutes, and the microsomal pellet was collected. The pellet was sonicated and centrifuged at 100, 000×g for 3 hours through either a step gradient of 5 to 30% sucrose in PBS, or through a 30% sucrose cushion. Fractions collected were dialyzed against PBS before testing.

Mouse immunizations and challenge. Groups of ten, 4–6-week old female BALB/c mice (Jackson Laboratories, Bar Harbor, Me.) were immunized subcutaneously with doses of 0.4, 1.0 and 4.0 μg of purified rEgp in 0.5 ml without adjuvant or with antigen adsorbed onto Alhydrogel (Alum, Superfos Biosector, Denmark). A control group of 10 mice was immunized with either PBS or $10^4$ plaque forming units (pfu) of DEN-2 virus (NGC strain). After 28 days, animals were boosted once with antigen, PBS or virus. Two weeks following the boost, half of the mice of each group were bled and individual sera were tested in plaque reduction neutralization assays. The other half of the mice of each group were challenged intracerebrally with $10^4$ pfu of DEN-2 virus (NGC strain). After 5 days, mice were sacrificed, brains were aseptically removed, homogenized and used in a plaque assay to quantitate viral growth.

Plaque reduction neutralization test (PRNT) and viral plaque assay. Mice were immunized on days 0 and 30 and bled 2 weeks following the boost. Sera collected from immunized mice at days were serially diluted ten-fold and incubated at 37° for 1 hour with 250 pfu/ml of DEN-2 virus (NGC strain). Following incubation, 2 ml aliquots of the sera-virus mixture was distributed onto duplicate monolayers of Vero cells in 6-well plates. After plates were rocked for 1 hour at 37° C., monolayers an overlay of 1% melted agarose in 2× EMEM was added onto each monolayer. After 6 days of incubation at 37° C., a second overlay of agarose containing a neutral red stain was applied, and plates were incubated overnight at 37° C. Viral plaques were counted the following day.

To quantitate viral growth, brain tissue homogenates serially diluted ten-fold were distributed onto Vero cell monolayers and incubated as described above. A garose overlays were added and viral plaques were counted as describe above.

RESULTS

Construction of recombinant pBlueBacIII transfer vector. The DEN-2 Egp gene fragment that was inserted into pBlueBacIII shown in FIG. 1. The fragment encodes the full Egp (495 amino acids) and 31 amino acids of the C terminus of the adjacent upstream M/preM protein. This segment serves as a signal for membrane translocation of the Egp (Markoff, L. J. Virol. 1989, 63:3345–3352)). Synthetic primers used to amplify the gene fragment each contained 18 nucleotides complementary to specific sequences in the DEN-2 E gene. The forward primer contains a Bgl II enzyme restriction site and an ATG start codon (SEQ ID NO:3). The reverse primer contains a Pst I enzyme restriction site and a stop codon. The E gene fragment was cut with Bgl II and Pst I enzymes and inserted unidirectionally into the BglII-Pst I cloning site of the pBlueBac III plasmid placing the recombinant gene was under the control of the AcNPV polyhedrin promoter.

Antigenicity of baculovirus-vectored rEgp. To perform an epitope analysis of the rEgp, the protein suspension containing rEgp and purified DEN-2 virus were reacted in an antigen dot blot assay with a panel of mAbs. The panel contained mAbs that bind either linear or discontinuous antigenic sites, and recognize both neutralizing and non-neutralizing epitopes. Results of the assay showed that the rEgp reacted to every mAb in the panel (Table 1). Since reactivities by this assay were quantitatively different for individual epitopes, binding affinities of the individual mAbs to the rEgp and native Egp were determined. The mAbs selected for affinity assays, 2H3, 4G2, and 9D12, demonstrated weak (2H3) to strong (9D12) binding to the rEgp in the antigen dot blot assay. Table 2 shows that the binding affinities of individual mAbs for rEgp and partially purified rEgp was comparable to their affinities for virus. Binding assays conducted at both neutral and slightly acidic pH demonstrated that these epitopes were not affected by pH.

TABLE 1

Antibody binding of the dengue-2 recombinant envelope protein expressed by baculovirus

| Antibody[a] | Reactivity with antigen[b] | | | |
|---|---|---|---|---|
| | ACNPV-E | ACNPV-prME | DEN-2 Virus | ACNPV |
| 3H5[d] | 13.6[c] | 10.1 | 7.5 | 1.4 |
| 9D12[d, e] | 12.3 | 12.1 | 9.0 | 1.0 |
| 13B7 | 10.5 | 4.1 | 5.6 | 3.6 |
| 4E5[d] | 8.6 | 6.6 | 10.5 | 1.0 |
| 2H3[d] | 4.9 | 2.5 | 11.5 | 1.9 |
| 4G2[d, e] | 8.5 | 5.0 | 16.8 | 1.0 |
| 1B7[d, e] | 5.1 | 3.1 | 8.9 | 1.2 |
| HMAF | 13.5 | 17.6 | 7.0 | 1.2 |
| HCS | 12.5 | NT | 12.5 | 1.6 |

[a]Antibodies were diluted 1:100 (mAbs) or 1:500 (anti-DEN-2 hyperimmune mouse ascites fluid, HMAF; or convalescent human sera, HCS).
[b]Antigenicity reactivity of extracts from High-5 cells infected with recombinant baculovirus clones containing DEN-2E (ACNPV-E) or prME (ACNPV-prME) genes, tested by antigen dot blot assay. Purified DEN-2 virus served as the positive control in the assay. Protein extracted from High-5 cells infected with wild-type baculovirus served as the negative control.
[c]Antigen-antibody biding was detected by $^{125}$I-labeled goat anti-mouse immunoglobulin. Data for each mAb and HMAF represents an average of three separate experiments; and for HCS, one experiment. Results are give as cpm × $10^3$.
[d]Antibodies which neutralize virus infectivity in vitro (Henchal et al. Am J. Trop. Med. Hyg. 1985, 34:162–167).
[e]Antibodies which recognize conformational epitopes (Henchal et al. Am J. Trop. Med. Hyg. 1985, 34:162–167; Megret et al. Virology, 1992, 187:480–491).

TABLE 2

Binding affinity of monoclonal antibodies to recombinant and native dengue-2 envelope proteins
Affinity binding of mAbs 9D12, 2H3, and 4G2 at pH 5.0

| Antigen[a] | 9D12 | 2H3 | 4G2 |
|---|---|---|---|
| Purified | $0.4 \times 10^{-6}$ | $3.2 \times 10^{-6}$ | $2.3 \times 10^{-6}$ |
| Lysate | $0.5 \times 10^{-6}$ | $1.0 \times 10^{-6}$ | $2.9 \times 10^{-6}$ |
| Virus | $5.2 \times 10^{-6}$ | $2.0 \times 10^{-6}$ | $1.3 \times 10^{-6}$ |

[a]Antigens were either partially-purified recombinant E protein, lysates of cells infected with the E-protein recombinant baculovirus, or purified DEN-2 virus.

Analysis of the antigenic properties of the full DEN-2 rEgp expressed in this study by baculovirus demonstrated that properly conformed proteins can be produced in this system. This was evidenced by the strong reactivity of the rEgp with mAbs that represented both linear and conformational-dependent epitopes within the native protein. Binding affinities of selected mAbs to native epitopes were not modified in the recombinant protein.

The mAb binding assays qualitatively demonstrate that native protein epitopes were preserved on the recombinant E protein.

Gel filtration analysis of DEN-2 rEgp particles. The DEN-2 Egp was expressed from baculovirus in High-five and Sf-21 cells. Cells were lysed by sonication in PBS containing 0.1% sarkosyl. Gel filtration of the cell lysates shows that the majority of rEgp produced by baculovirus had self-aggregated to form high molecular weight particles. Protein separation profiles for infected cell lysates are shown in FIGS. 2, 3, 4 and 5. Antigenic reactivity with anti-DEN-2 HMAF is distributed among nearly all fractions passed through G-100 Sephadex, with a major antigenic peak eluting at the position of calibration standard thyroglobulin, molecular weight (mol wt) 670 kilodaltons (kd). Similar results were obtained for gel FPLC using Superose 6 (FIG. 3) and Superose 12 (FIGS. 4 and 5). The rEgp was eluted in the void volume of the Superose 6 column (molecular weight exclusion, $5\times10^6$ kd) in fractions 8 through 11 compared to the calibration standard thyroglobulin which was eluted in fractions 13 and 14. Similarly, the rEgp eluted in the void volume of the Superose 12 column (mol wt exclusion, $3\times10^5$).

The role of sarkosyl and sonication in disruption of rEgp particles was also examined during Superose 12 chromatography. By equilibrating column in increasing amounts of sarkosyl (0.1 to 3.0%), protein elution profiles were shifted, however position major antigenic peak associated with rEgp was not altered by sarkosyl (FIGS. 4A, B, C, D). Sonication for up to 30 minutes did, however, partially disrupt rEgp aggregates as well as other high molecular weight protein aggregates (FIGS. 5A, B, and C).

Purification of E particles. Gel filtration results indicated that rEgp aggregates could be separated from the majority of cellular proteins based on their large size. However, yield of partially purified rEgp produced in this manner were relatively low and the process was slowed by frequent necessity to clean the column matrix. Aggregated rEgp particles were therefore purified from other cellular components by differential centrifugation using a sucrose cushion. In initial experiments, the microsomal fraction of infected cell lysates was collected by ultracentrifugation, sonicated, and centrifuged through a 5–30% sucrose step gradient. Fractions containing 500 μl were concentrated, dialyzed and analyzed for reactivity with anti DEN-2 mouse HMAF. FIG. 6 shows that very high antigenic activity was present in the gradient pellet, compared to relatively small amount of antigenic activity that was distributed into several gradient fractions. Since the majority of E antigen was present in the 5–30% sucrose gradient pellet, E protein aggregates were purified by centrifugation of the microsomal fraction through a 30% sucrose cushion.

SDS-polyacrylamide gel electrophoresis and western blotting. Proteins that were pelleted through the 30% sucrose cushion were analyzed by SDS-PAGE and western blotting. As shown in FIG. 7A, this pellet contained three protein bands that stained with Coomassie blue on a 10% reduced SDS-polyacrylamide gel. A western blot of a non-reduced 10% gel loaded with identical samples revealed three antigenic bands that appear to correspond to the three protein-stained bands (FIG. 7B). These bands seen on the protein gel and on the blot migrate close together, and are likely to represent varying degrees of glycosylation of the rEgp.

Immunogenicity of the purified rEgp. The purified rEgp particles were tested in immunogenicity trials in mice. Previously it was shown that a cellular lysate containing baculovirus vectored rEgp was fully reactive with native E-specific monoclonal antibodies and induced a low titer of neutralizing antibody in mice. Table 3 shows results from immunization of mice with purified rEgp. Mice responded to immunization by production of neutralizing antibodies. Table 3 shows that a non-adjuvanted immunizing dose of 4 μg induced production of neutralization antibodies. This response was boosted several fold when rEgp was pre-adsorbed to Alum, and was equivalent to titers induced by live virus. The pre-absorption to alum also increased the response with 1 μg to a detectable level (Table 3).

TABLE 3

$PRNT_{50}$ in mice immunized with baculovirus expressed DEN-2 E protein

| rEgp with Alum | | rEgp/no adjuvant | | | |
|---|---|---|---|---|---|
| Dose 4 μg | Dose 1 μg | Dose 4 μg | Dose 1 μg | DEN-2 NGC | Control |
| >850 | 458 | 472 | <13 | 633 | <13 |
| >850 | 280 | 233 | <13 | 526 | <13 |
| 441 | 473 | 538 | <13 | 480 | |
| >850 | 476 | 261 | <13 | 622 | |
| 540 | 788 | 23 | ND | 574 | |

*Vaccination schedule: Day 1 and day 30. Bled two weeks after the second dose.

Mice immunized with purified non-adjuvanted and adjuvanted rEgp were tested in a challenge assay with live virus. Table 4 shows results for growth of DEN-2 challenge virus in immunized and control mice.

TABLE 4

Percent protection measured by reduction of dengue virus in the brains of immunized, intracerebrally challenged mice

| Immunization[1] | Percent reduction[2] |
|---|---|
| 4 μg with alum | 88.5 ± 35.1 |
| 1 μg with alum | 97 ± 4.2 |
| 0.25 μg with alum | 92.6 ± 5.1 |
| 4 μg without alum | 83.4 ± 40.2 |
| 1 μg without alum | 78.5 ± 24.7 |
| 0.25 μg without alum | 96.8 ± 3.8 |
| live virus | 100 ± 0 |
| none | 0 ± 86 |

[1]Mice were immunized at days 0 and 30 with indicated amounts of recombinant dengue 2 envelope protein or with live dengue 2 virus. Control mice were not immunized.
[2]Mice were inoculated intracerebrally with 10,000 pfu of mouse adapted dengue 2 virus two weeks after the last immunization. Five days later, mice were euthanized and the brains removed for quantitation of dengue virus in the brain. The percent reduction was calculated by multiplying 100 times the formula (control-plagues/control) where control is the mean of the virus plaques in un immunized mice and plaques isthe plaques measured in individual mice. Results are displayed as the mean ± the standard deviation for the mice in each group.

Table 4 shows that the mean number of viral plaques obtained from brains of all groups of immunized mice were greatly reduced compared to that obtained in unimmunized mice. Mean number of plaques obtained for mice immunized with adjuvanted antigen (groups 1, 2 and 3 mice, immunized with 4, 1, and 0.4 μg of rEgp, respectively), were significantly lower than those obtained for mice immunized with non-adjuvanted rEgp.

What is claimed is:

1. An isolated and purified dengue virus DNA fragment consisting essentially of a DNA fragment which encodes a complete dengue virus envelope protein and a carboxy terminus segment of premembrane protein which comprises a translocation signal for said Envelope protein.

2. The isolated and purified DNA fragment according to claim 1, wherein said dengue virus is dengue 2.

3. The DNA fragment of claim 2 which encodes 495 amino acids of said envelope protein and 31 amino acids of said carboxy terminus segment of premembrane protein, said fragment comprising the nucleotide sequence specified in SEQ ID NO: 1 or an allelic variant which retains the neutralizing antibody production characteristic of a protein encoded by SEQ ID No. 1.

4. The DNA fragment according to claim 3, wherein said DNA fragment encodes the amino acid sequence specified in SEQ ID NO: 2.

5. The isolated and purified DNA fragment according to claim 1, wherein said dengue is dengue 1.

6. The isolated and purified DNA fragment according to claim 1, wherein said dengue is selected from the group consisting of dengue 3 and dengue 4.

7. A recombinant DNA construct comprising:
   (i) a vector, and
   (ii) an isolated and purified dengue virus DNA fragment according to claim 1.

8. A recombinant DNA construct according to claim 7, wherein said dengue virus is dengue 2.

9. The recombinant DNA construct according to claim 7, wherein said vector is a eukaryotic expression vector.

10. The recombinant DNA construct according to claim 8, wherein said vector is a eukaryotic expression vector.

11. A recombinant DNA construct comprising:
    (i) a vector, and
    (ii) a dengue 2 DNA fragment according to claim 3.

12. The recombinant DNA construct according to claim 11, wherein said vector is a eukaryotic expression vector.

13. The recombinant DNA construct according to claim 11, wherein said DNA fragment encodes the amino acids sequence specified in SEQ ID NO: 2.

14. The recombinant DNA construct according to claim 11 wherein said vector is pBlueBacIII.

15. A host cell transformed with a recombinant DNA construct comprising:
    (i) a vector, and (ii) an isolated and purified dengue virus DNA fragment according to claim 1.

16. A host cell according to claim 15, wherein said cell is prokaryotic.

17. The host cell according to claim 15, wherein said cell is a eukaryotic cell.

18. A method for producing a dengue virus recombinant protein particle, said method comprising the steps of:

(i) culturing a host cell transformed with an expression vector according to claim 9 under conditions such that said DNA fragment is expressed and said recombinant protein is produced as a particle, said particle comprising more than one unit of said recombinant protein; and (ii) isolating said recombinant protein particle.

19. The method according to claim 18, wherein said dengue virus is dengue 2.

20. The method of claim 18 wherein isolating said recombinant protein particle comprises:

(i) pelleting said cells by centrifugation, (ii) separating the cell pellet and the supernatant, (iii) lysing said cell pellet to release said recombinant protein particle;

(iv) isolating said recombinant protein particle of step (iii);

(v) fractionating said recombinant protein particle of step (iv) on a gradient; and (vi) isolating said recombinant protein particle, in a purified form.

* * * * *